United States Patent [19]

Dettmer et al.

[11] Patent Number: 4,760,202
[45] Date of Patent: Jul. 26, 1988

[54] PROCESS FOR THE PRODUCTION OF TERTIARY ALCOHOLS

[75] Inventors: Michael Dettmer, Dietzenbach; Gunther Osterburg, Rheurdt; Milan Prezelj, Frankfurt am Main; Werner Webers, Rheinberg, all of Fed. Rep. of Germany

[73] Assignee: Deutsche Texaco Aktiengesellschaft, White Plains, N.Y.

[21] Appl. No.: 86,429

[22] Filed: Aug. 18, 1987

[30] Foreign Application Priority Data

Aug. 19, 1986 [DE] Fed. Rep. of Germany ....... 3628008

[51] Int. Cl.$^4$ ............................................. C07C 29/04
[52] U.S. Cl. ................................................... 568/899
[58] Field of Search ......................................... 568/899

[56] References Cited

U.S. PATENT DOCUMENTS

| | | | |
|---|---|---|---|
| 4,012,456 | 3/1977 | Chaplits | 568/899 |
| 4,087,471 | 5/1978 | Bowman et al. | 568/899 |
| 4,180,688 | 12/1979 | Imaizumi et al. | 568/899 |
| 4,182,920 | 1/1980 | Giles et al. | 568/899 |
| 4,307,257 | 12/1981 | Sada et al. | 568/899 |
| 4,579,984 | 4/1986 | Neier et al. | 568/899 |

Primary Examiner—J. E. Evans
Attorney, Agent, or Firm—Robert A. Kulason; Robert B. Burns; James J. O'Loughlin

[57] ABSTRACT

Tertiary alcohols with 4 or 5 carbon atoms are produced by reacting an isoolefin-containing hydrocarbon stream with water in the presence of a strongly acidic, solid hydration catalyst in such a way that each of the two process streams, the hydrocarbon stream and the process water, is cascaded through several reactors connected in series such that one process stream is fed to one end of the line of reactors and the other process stream to the other end of the line of reactors, and the two process streams pass through the line of reactors in opposite directions, while they pass through the individual reactors as parallel currents.

12 Claims, 3 Drawing Sheets

PROCESS FOR THE PRODUCTION OF TERTIARY ALCOHOLS

BACKGROUND OF THE INVENTION

The instant invention relates to a process for the production of tertiary alcohols with 4 or 5 carbon atoms by reacting a tertiary olefin-containing hydrocarbon stream with water in the presence of a strongly acidic, solid hydration catalyst, preferably a strongly acidic cation exchange resin, removing the residual gas and recovering the aqueous alcohol.

DISCLOSURE STATEMENT

Processes for the production of tertiary alcohols by hydration of the corresponding olefinic unsaturated compound in the presence of cation exchange resins of the sulfonic acid type are known. Acceptable yields are obtained only by adding solvents as solubilizers to the water and tertiary olefin mixture to from an homogeneous phase and in providing, a higher concentration of the olefin in the process water. For instance, a process in which isobutene or an isobutene-containing hydrocarbon stream is reacted with an aqueous solution of an organic acid in the presence of an acidic cation exchange resin as catalyst is disclosed in DE-OS No. 24 30 470. A process in which a monovalent alcohol is added to the reaction system and a catalyst is disclosed in Japanese patent application No. 137906/75. According to U.S. Pat. No. 4,096,194, glycol, glycol ether, or glycol diether are added to the reaction mixture and JP-OS No. 59802/76 (Chemical Abstracts, Vol. 86, 1977, 86:19392 b) discloses a reaction in the presence of polar solvents, e.g. dioxane.

DE-OS No. 30 29 739 discloses the use of polyhydric alcohols of the neopentyl type and DE-OS No. 27 21 206 and DE-OS No. 30 31 702 discloses sulfones, e.g. Sulfolan, as solubilizers.

The noted processes for the production of tertiary alcohols have the disadvantage of giving rise to the formation of byproducts, such as addition products ex isobutene and the organic acids or organic solvents added. Since the boiling points of the by-products and of the added solvents are close to or below that of tertiary butyl alcohol, it is difficult to separate them and to isolate the tertiary butanol from these byproducts and solvents. While the process according to DE-OS No. 27 21 206 for the production of sec-butanol by reaction of butene-1 and butene-2 at a temperature of 100° to 220° C. shows good stability of the solvent used, it is impossible to produce tertiary butanol in a high yield by selective hydration of isobutene, because the n-olefins which are also present react with water and a larger portion of sec-butyl alcohol and isobutene dimers is formed besides tertiary butyl alcohol. When using organic acids, e.g. acetic acid, measures for inhibiting corrosion have to be taken.

DE-AS No. 11 76 114 discloses a process performed without solubilizers but which result in lower conversions or selectivities. DE-OS No. 30 31 702 shows in Table 2, page 14 that without a solubilizer economic isobutene conversions are hardly attainable.

It is the object of this invention to provide a process for the production of tertiary alcohols in good yields and selectivities by the direct hydration of tertiary olefin without the addition of solubilizers and the disadvantages attaching thereto.

SUMMARY OF THE INVENTION

In accordance with this invention, tertiary alcohols having 4 or 5 carbon atoms are prepared by reacting an isoolefin-containing hydrocarbon stream with water in the presence of a strongly acidic solid hydration catalyst at 30° to 150° C., a reaction pressure of 10 to 50 bar and a water/tertiary olefin mole ratio of 20–150:1, removing the residual gas the recovering the aqueous alcohol, characterized by cascading the hydrocarbon stream and the process water through several reactors connected in a series such that one process stream is charged to one end of the line of reactors and the other process stream is charged to the other end of the line of reactors and the two process streams flow through the line of reactors in opposite directions, while they flow through the individual reactors as parallel currents.

DETAILED DESCRIPTION OF THE INVENTION

Figure 1:
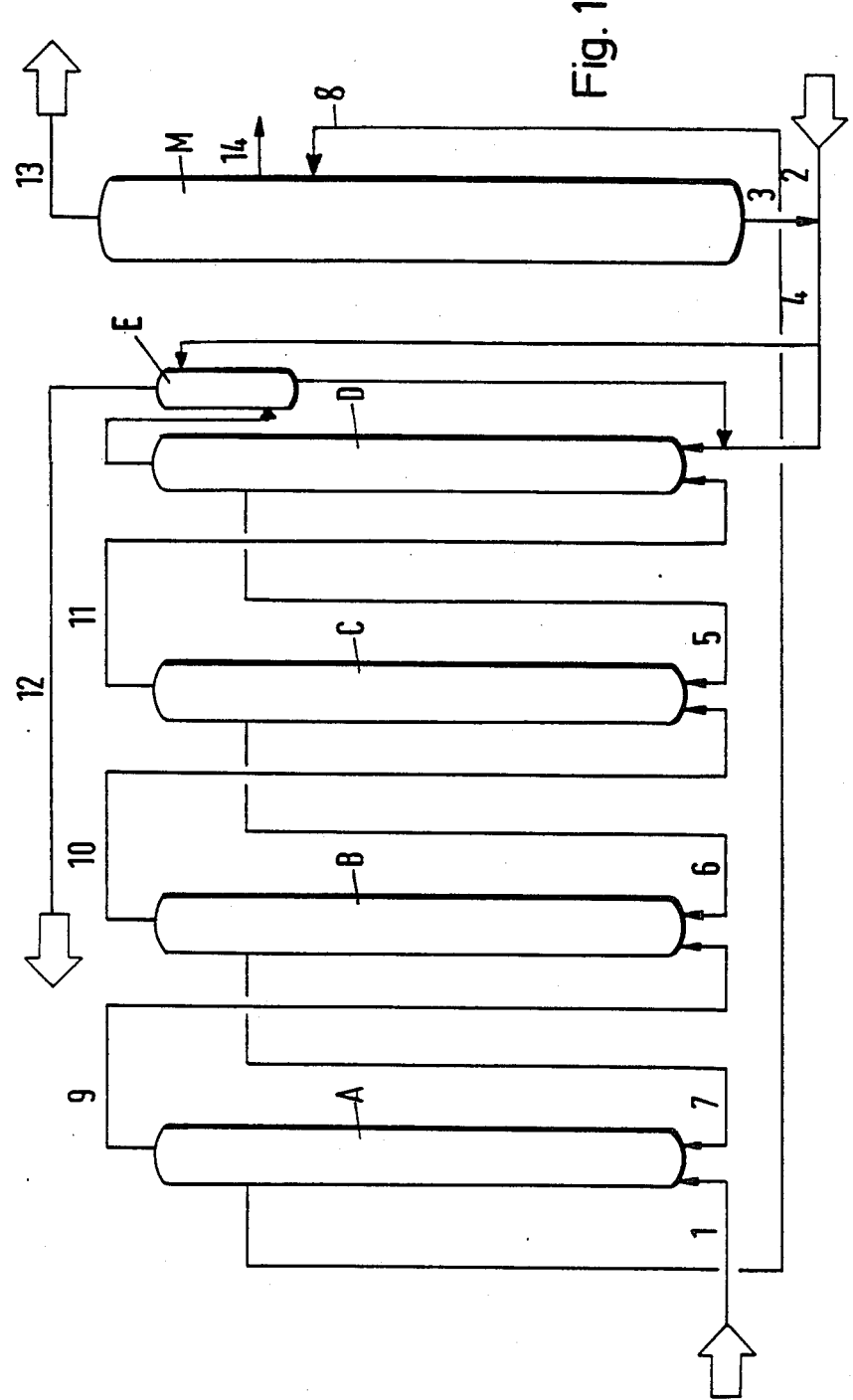

The present invention provides a process for the production of $C_4$ and $C_5$ aliphatic alcohols in which a $C_4$ or $C_5$ olefin or a $C_4$ or $C_5$ olefin-containing hydrocarbon mixture is reacted with water in the presence of a hydration catalyst, particularly of a cation exchange resin of the sulfonic acid type. The process is conducted by charging the olefin-containing hydrocarbon stream to the inlet of the first reactor and the process water to the inlet of the last reactor in a series of two or more reactors. In the individual reactors, the process water and the hydrocarbon stream form parallel currents, but relative to the entire reactor system, the hydrocarbon stream flows or is cascaded from the first reactor to the last one while in countercurrent thereto the process water flows or is cascaded from the last reactor to the first.

Either sump operation in which the hydrocarbon stream and the process water are fed to the sump of the respective reactors, or trickle operation in which the two process streams are fed to the top of the respective reactors is possible. The process of the invention is preferably performed in a reactor system consisting of 2 to 10 reactors, particularly 3 to 5.

Following the same mode of operation, the process of the invention can also be performed in a single reactor having several reactor beds as separate reaction zones, one process stream being led from the top to the bottom and the other process stream being led from the bottom to the top, and while in the sump phase process the process streams are fed to the sump of the respective zone and in the trickle process they are fed to the top of the respective zone, the individual reaction zones are flown through by parallel streams. In order to remove the alcohol, it is advantageous to wash the hydrocarbon stream leaving the reactor system and termed from hereon 'residual gas' with water in order to remove the alcohol and to charge this water thereafter as process water or as a part thereof.

When the tertiary alcohol is made azeotropic, the secondary alcohol formed as a byproduct can be removed from the predewatering column as a lateral stream which is withdrawn particularly few trays, preferably 1 to 7 trays, above the tray for feeding aqueous alcohol. Hence it was found that high isobutene conversions and high selectivities can also be attained without addition of solubilizers, namely according to the process of the invention, isobutene conversions of more than 98% can be attained without using any solubilizers.

The selectivity of the process if 99 to 99.9%. After washing with water, the raffinate leaving the last reactor is practically free from alcohol.

Owing to the mode of operation, the process of the invention has the advantage over the known processes that the tertiary olefin is almost completely converted even if the hydrocarbon mixtures contain little isoolefin.

The instant invention provides a process for the production of tertiary alcohols, particularly tertiary butyl alcohol (TBA), in which a $C_4$ or $C_5$- isoolefin or an isoolefin-containing hydrocarbon stream, particularly isobutene or an isobutene-containing hydrocarbon stream, is preferably reacted with water in the presence of a strongly acidic cation exchange resin, particularly such of the sulfonic acid type. The process can be performed by charging the isoolefin-containing hydrocarbon stream to the sump of the first reactor and feeding the process water to the sump of the last reactor. In the individual reactors the process water stream and the hydrocarbon stream do form parallel currents, but the process water is cascaded from the last reactor to the first in opposite direction to the hydrocarbon stream flowing through the reactor system from the first reactor to the last one.

At the top of the first reactor an aqueous alcohol is withdrawn and the alcohol is obtained therefrom by distillation. The alcohol obtained has a purity of 99 to 99,9%, depending on the reaction conditions. Besides SBA the TBA obtained may contain minor quantities of dimeric compounds. Such diisobutenes are contained in the $C_4$ raffinate, but not in the TBA obtained from the water phase.

The process can also be performed as a trickle process according to the mode of operation of the invention. The isoolefin-containing hydrocarbon stream is then fed to the top of the first reactor. The process water is fed to the top of the last reactor, is withdrawn at the sump of this reactor, and is refed in opposite direction to the hydrocarbon stream to the top of the next reactor. By phase separation in the individual reactors the aqueous phase obtained can be withdrawn and charged to the next reactors. The aqueous crude alcohol is finally obtained in the sump of the first reactor and is worked up by distillation. From the sump of the last reactor a residual gas is withdrawn that contains only little isobutene.

Owing to the countercurrent operation, the process of the invention has yet one more advantage, besides high olefin conversions and high selectivity, over the known processes leading the process streams as parallel currents through the reactor system consisting of one or more reaction zones. Since the TBA distribution equilibrium between aqueous phase and hydrocarbon phase is about 1:3.5 under the reaction conditions chosen, the residual gas has a high TBA content (12 to 30%) when performing the operation in parallel flow according to the prior art. Therefore, to separate the TBA from the residual gas multistage extraction or distillation would be necessary. In the process of the invention the residual gas leaving the last reactor contains only 0.2 to 2.5% TBA. By subsequent washing with process water or part thereof (for instance in a countercurrent reactor) a practically TBA-free residual gas can be obtained (less than 0.1% TBA). The TBA is separated from the process water in a distillation column, an azeotropic TBA containing 12% water being obtained at the top of the column and excess process water being withdrawn at the sump of the column and being recycled to the last reactor.

Apart from the above, the process of the invention is performed under conventional conditions. The temperature is 30° to 150° C., preferably 60° to 110° C. The reaction pressure is 10 to 50 bar, preferably 10 to 20 bar. The total LHSV is 0.2 to 5 hours$^{-1}$, preferably 0.2 to 2 hours$^{-1}$. The water/isobutene mole ratio is 20-150:1, preferably 40-90:1.

Examples of the embodiment of the invention are shown in the drawings and are described in detail in the following.

The figures show:

FIG. 1 Flowsheet of the sump process of the invention.

Figure 2:
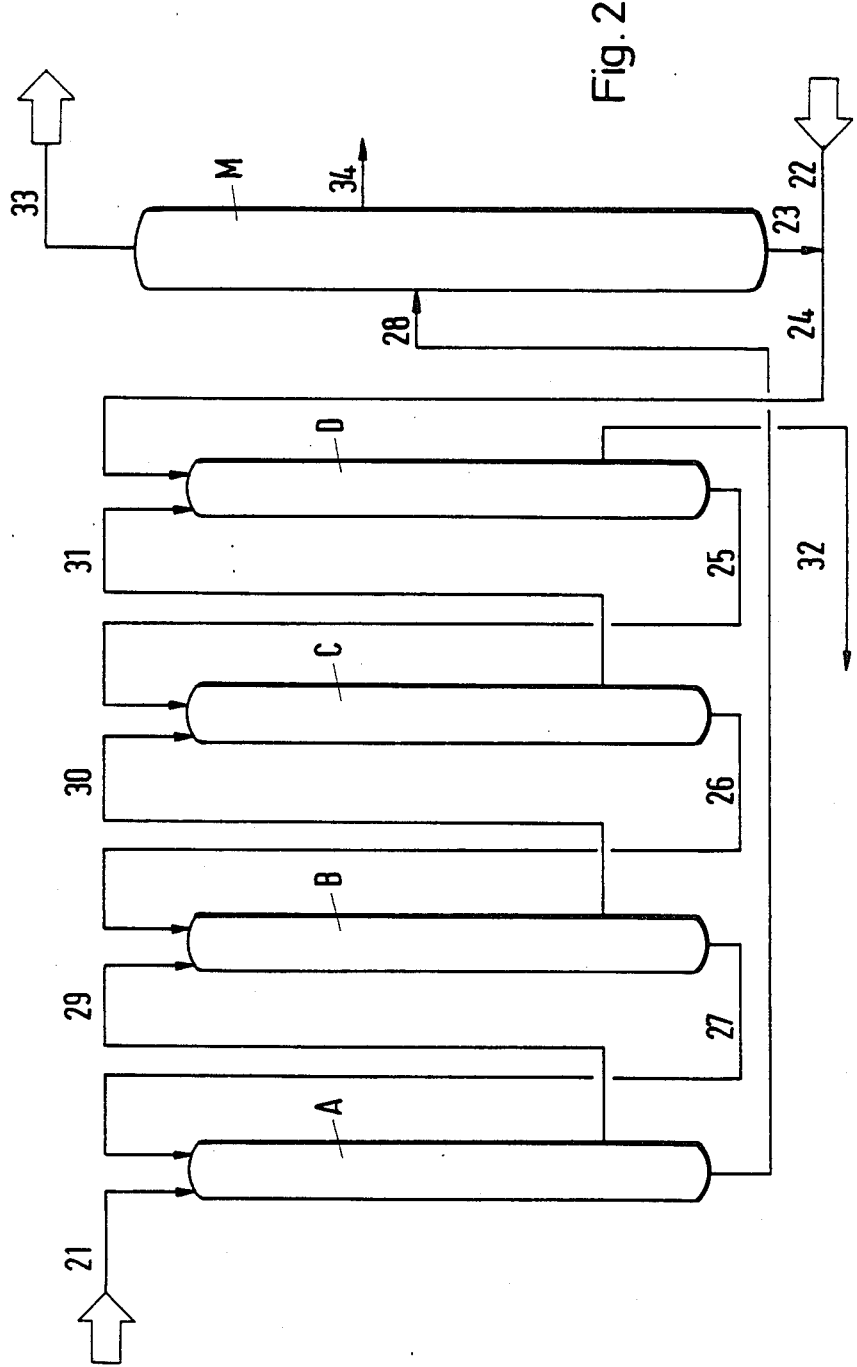

FIG. 2 Flowsheet of the trickle process of the invention.

Figure 3:
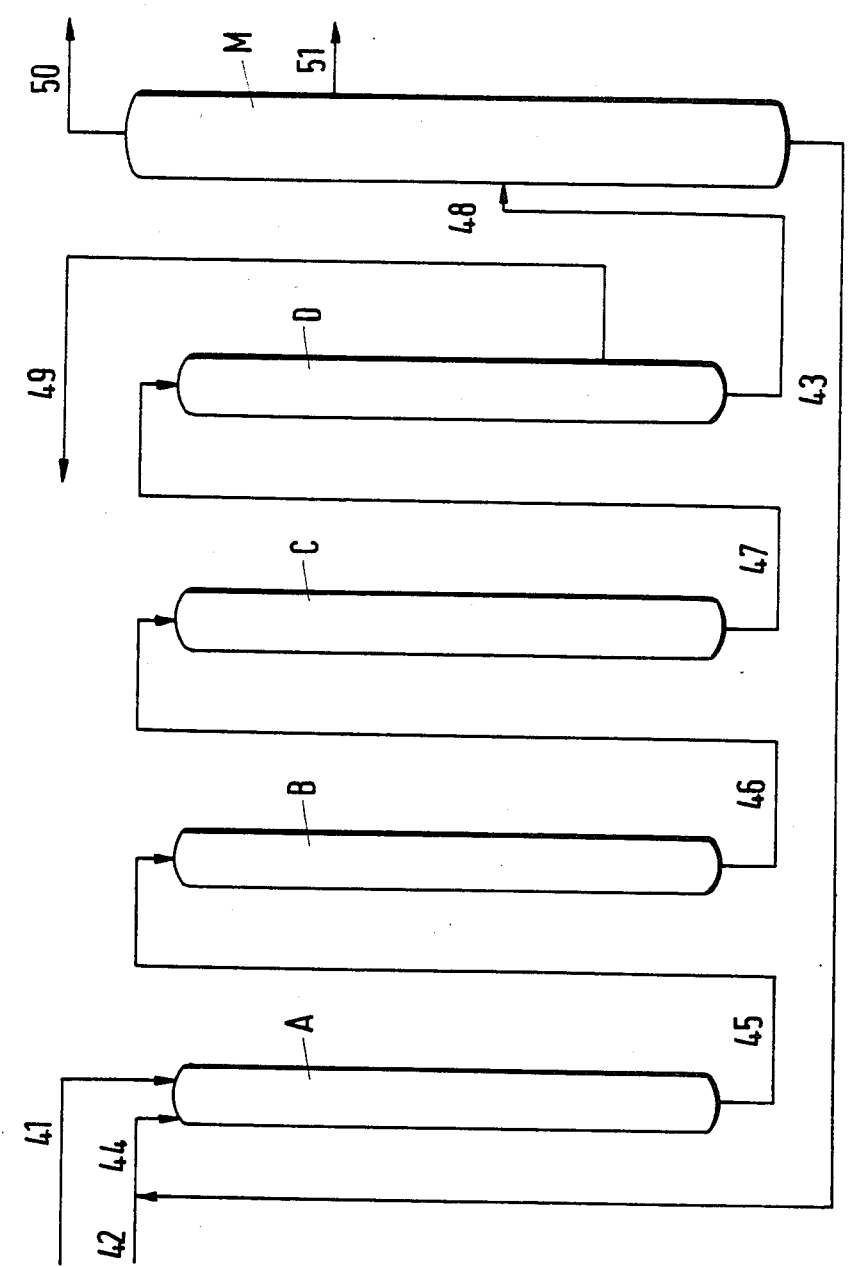

FIG. 3 Flowsheet of the parallel current trickle process according to the prior art.

In a sump process according to FIG. 1 with a reactor system consisting of 4 reactors A, B, C, D an isobutene-containing hydrocarbon mixture ($C_4$ cut) is fed through line 1 to the sump of reactor A. Process water is united through line 2 with the excess water from the sump of column M (line 3) and is fed through line 4 and, wholly or in part, via extractor E to the sump of reactor D. The aqueous phase withdrawn through line 5 in the top zone of reactor D is fed to the sump of reactor C, is led through lines 6 and 7 to the subsequent reactors B and A, resp., and is finally led through line 8 to column M.

The hydrocarbon stream withdrawn through line 9 at the top of reactor A is fed to the sump of reactor B, is then fed through lines 10 and 11 to the reactors C and D, resp., and is finally removed through line 12 as residual gas that has previously been washed in extractor E in order to eliminate the TBA contained therein. To this end the process water from line 4 or part of the process water stream from line 4 is used which is then fed together with the residual process water as described to the sump of reactor D.

Thus, the process water and the tertiary olefin-containing hydrocarbons are led through the individual reactors as parallel currents, but they are cascaded through the line of reactors as counterflows.

The process of the invention can also be performed as a countercurrent trickle process. An embodiment is depicted in FIG. 2 using the same reactor system with 4 reactors. In this process the isoolefin-containing hydrocarbon mixture is fed through line 21 to the top of reactor A, while the process water is fed through line 24 to the top of reactor D, and the process streams are cascaded as countercurrents through the reactor system.

The process water charged to reactor D is withdrawn as an aqueous phase through line 25, is charged to the top of reactor C, and is then fed through lines 26 and 27 to the reactors B and A, respectively. Accordingly, the hydrocarbon stream is withdrawn in the opposite direction in the sump zone of reactor A and is charged through the lines 29, 30, 31 to the reactors B, C, D, resp., and is finally removed through line 32 as residual gas which is washed in extractor E in order to remove the TBA contained therein.

Aqueous TBA is withdrawn through lines 8 and 28, resp., either in the top zone (sump process) or at the sump (trickle process) of reactor A and is fed to column M, azeotropic TBA that may contain besides 12% water 0.05 to 1% SBA and slightest amounts of dimeric compounds being obtained at the top of the column through line 13 or 33. If required, the azeotropic alcohol can be dried in the known way.

According to a preferred embodiment of the process, the reaction temperature in four reactors connected in series is increased such that almost complete conversion of isobutene and an about 99% selectivity are attained even if the water load is low.

The purity of the formed TBA that is deteriorated by the formation of sec-butyl alcohol can be improved up to 99.9% if at a suitable spot of the azeotrope-forming column and under the conditions used for the distillative working-up of aqueous crude TBA the SBA which is reconcentrated with respect to the TBA quantity is withdrawn through line 14 or 34 as a water-containing lateral stream.

In the process of this invention olefin and water in counterflow are cascaded through the reaction zones. Using this process, the disadvantages of parallel flow operation, namely requirement of high olefin concentration in the feed gas insufficient olefin conversion poor selectivity can be overcome making aftertreatment superfluous.

The advantages of the counterflow operation according to the process of this invention can be achieved not only when a new plant is erected or when an existing parallel flow process is completely revamped, but also by conversion of existing parallel flow reactors in counterflow reactors or by adding 2 or more counterflow reactors where the residual gas discharged from the parallel flow reactors and still laden with a great quantity of olefins and byproducts is converted such that an olefin conversion of 98 to 99%, a selectivity of 99%, and a satisfactory reactor efficiency are attained without aftertreatment.

Thus, the same objective as with a separate counterflow process is attained, but with less investment.

For the combined parallel flow/counterflow process any solid catalyst system suitable for the direct hydration of olefins can be used. It is also possible to combine other catalyst systems used in parallel flow processes with the acidic cation exchange resin preferred here in the counterflow process.

EXAMPLES 1 THROUGH 6

In the process depicted in FIG. 1 in which a total of 2,750 g of a commercial strongly acidic cation exchange resin were distributed over four reactors, a isobutene-containing $C_4$-hydrocarbon mixture was fed via line 1. The process water charged via stream 4 passed through the reactors as a cascade from the last reactor to the first. Materials flows, operating conditions, and results have been compiled in Table 1.

TABLE 1

|  |  | Examples |  |  |  |  |  |
|---|---|---|---|---|---|---|---|
|  |  | 1 | 2 | 3 | 4 | 5 | 6 |
| Temperature, | °C. | 70 | 92 | 92 | 92 | 92 | 98 |
| Pressure | bar | 16 | 16 | 16 | 16 | 16 | 16 |
| Isobutene content, | mole % | 45 | 45 | 45 | 78.5 | 17 | 45 |
| n-Butenes content, | mole % | 40 | 40 | 40 | 8 | 58 | 40 |
| Butanes, | mole % | 15 | 15 | 15 | 3.5 | 25 | 15 |
| Process water quantity (Stream 4), | g/h | 8000 | 8000 | 4000 | 4000 | 4000 | 4000 |
| Wash water quantity | g/h | 2000 | 2000 | 2000 | 2000 | 2000 | 2000 |
| $C_4$ hydrocarbon quantity (Stream 1), | g/h | 600 | 600 | 600 | 600 | 600 | 600 |
| Isobutene quantity, | mole/h | 4.8 | 4.8 | 4.8 | 8.4 | 1.8 | 4.8 |
| Isobutene conversion, | mole % | 86 | 98.5 | 92 | 96 | 90 | 98 |
| n-Butenes conversion, | mole % | 0.09 | 1.0 | 0.9 | 0.3 | 1.2 | 1.3 |
| Selectivity for TBA, | mole % | 99.9 | 99.1 | 99.1 | 99.7 | 98.8 | 98.7 |
| Selectivity for SBA, | mole % | 0.09 | 0.9 | 0.9 | 0.3 | 1.2 | 1.3 |
| Selectivity for dimeric compounds, | mole % | 0.015 | 0.02 | 0.02 | 0.025 | 0.015 | 0.025 |
| TBA in residual ga, (Stream 12), | wt. % | <0.1 | <0.1 | <0.1 | <0.1 | <0.1 | <0.1 |

EXAMPLES 7 THROUGH 12

The examples 1 through 6 were repeated, the difference being that the quantity of strongly acidic cation exchange resin was distributed over three reactors. Operating conditions, materials flows, and results have been compiled in Table 2.

TABLE 2

|  |  | Examples |  |  |  |  |  |
|---|---|---|---|---|---|---|---|
|  |  | 7 | 8 | 9 | 10 | 11 | 12 |
| Temperature, | °C. | 70 | 92 | 92 | 92 | 92 | 98 |
| Pressure, | bar | 16 | 16 | 16 | 16 | 16 | 16 |
| Isobutene content, | mole % | 45 | 45 | 45 | 78.5 | 17 | 45 |
| n-Butenes content, | mole % | 40 | 40 | 40 | 8 | 58 | 40 |
| Butanes, | mole % | 15 | 15 | 15 | 3.5 | 25 | 15 |
| Process water quantity (Stream 4), | g/h | 8000 | 8000 | 4000 | 4000 | 4000 | 4000 |
| Wash water quantity | g/h | 2000 | 2000 | 2000 | 2000 | 2000 | 2000 |
| $C_4$ hydrocarbon quantity (Stream 1), | g/h | 600 | 600 | 600 | 600 | 600 | 600 |
| Isobutene quantity, | mole/h | 4.8 | 4.8 | 4.8 | 8.4 | 1.8 | 4.8 |
| Isobutene conversion, | mole % | 76 | 90 | 86 | 88 | 82 | 89 |
| n-Butenes conversion, | mole % | 0.09 | 0.9 | 0.8 | 0.3 | 1.1 | 1.1 |
| Selectivity for TBA, | mole % | 99.9 | 99.0 | 99.0 | 99.6 | 98.7 | 98.9 |
| Selectivity for SBA, | mole % | 0.1 | 1.0 | 1.0 | 0.35 | 1.3 | 1.1 |
| Selectivity for | mole % | 0.015 | 0.02 | 0.02 | 0.025 | 0.02 | 0.02 |

TABLE 2-continued

|  |  | Examples | | | | | |
| --- | --- | --- | --- | --- | --- | --- | --- |
|  |  | 7 | 8 | 9 | 10 | 11 | 12 |
| dimeric compounds, TBA in residual gas, (Stream 12), | wt. % | <0.1 | <0.1 | <0.1 | <0.1 | <0.1 | <0.1 |

EXAMPLES 13 THROUGH 15

The examples 13 through 15 were carried out according to the trickle process depicted in FIG. 2 in which the four reactors were filled with a total of 2,750 g of the strongly acidic cation exchange resin. Materials flows, operating conditions, and results have been compiled in Table 3.

TABLE 3

|  |  | Examples | | |
| --- | --- | --- | --- | --- |
|  |  | 13 | 14 | 15 |
| Temperature, | °C. | 70 | 92 | 98 |
| Pressure, | bar | 16 | 16 | 16 |
| Isobutene content, | mole % | 45 | 45 | 45 |
| n-Butenes content, | mole % | 40 | 40 | 40 |
| Butanes, | mole % | 15 | 15 | 15 |
| Process water quantity (Stream 24), | g/h | 8000 | 8000 | 4000 |
| Wash water quantity, | g/h | 2000 | 2000 | 2000 |
| $C_4$ hydrocarbon quantity (Stream 21), | g/h | 600 | 600 | 600 |
| Isobutene quantity, | mole/h | 4.8 | 4.8 | 4.8 |
| Isobutene conversion, | mole % | 87.5 | 98.7 | 98.5 |
| n-Butenes conversion, | mole % | 0.2 | 1.0 | 1.5 |
| Selectivity for TBA, | mole % | 99.8 | 99.0 | 98.5 |
| Selectivity for SBA, | mole % | 0.2 | 1.0 | 1.5 |
| Selectivity for dimeric compounds, | mole % | 0.03 | 0.05 | 0.05 |
| TBA in residual gas, (Stream 32), | wt. % | 0.1 | 0.1 | 0.1 |

EXAMPLE 16

In a process depicted in FIG. 1 in which the reactors were filled with a total of 2,750 g of the commercial strongly acidic cation exchange resin 600 g/h of a 45 mole % isobutene containing $C_4$ hydrocarbon mixture and 8,000 g/h of process water were charged through line 1 and line 4, resp., and were cascaded in counter-current operation through the reactors according to example 1.

At an operating temperature of 70° C. and an operating pressure of 16 bar an isobutene conversion of 86% was attained. Accordingly, 8,232 g/h of aqueous reactor effluent containing 3.72 wt. % TBA, only traces of SBA and dimeric products were withdrawn through line 8.

In order to continuously distill the TBA, this aqueous reaction product was fed to the 12th tray of a column having a total of 50 trays. Using a feed quantity of 3,950 g/h of aqueous product 348 g/h of azeotropic TBA containing 12% water and having a purity of 99.9 wt. %, relative to anhydrous TBA, were withdrawn overhead. At the sump of the distillation column alcohol-free process water was recovered at a reflux/distillate reflux ratio of 2.

EXAMPLE 17

In a process depicted in FIG. 1 in which the reactors were filled with a total of 2,750 g of the commercial strongly acidic cation exchange resin 600 g/h of a 45 mole % isobutene containing $C_4$ hydrocarbon mixture and 4,000 g/h of process water were charged through line 1 and line 4, resp., and were cascaded in counter-current operation through the reactors according to example 6.

At an operating temperature of 98° C. and an operating pressure of 16 bar an isobutene conversion of 98% was attained. Accordingly, 4,270 g/h of aqueous reactor effluent containing 8.16 wt. % TBA, 0.1 wt. % SBA, and less than 0.01 wt. % dimers were withdrawn through line 8.

In order to continuously distill the TBA this aqueous reaction product was fed to the 12th tray of a column having a total of 70 trays. Using a feed quantity of 4,270 g/h of aqueous product 14.7 g/h of a product stream containing 29.2 wt. % SBA, 49.5 wt. % TBA, and 21.3 wt. % water were withdrawn through line 14 from the 17th tray located five trays above the product feeding tray. At the same time 387.9 g/h of distillate containing 11.96 wt. % water were obtained at the top of the column, the purity being 99.9 wt. %, relative to anhydrous TBA.

At the sump of the column alcohol-free process water was recovered at a reflux/distillate reflux ratio of 2.

EXAMPLES 18 THROUGH 20

(Comparison Examples)

For the comparison examples the four reactors were used for a parallel current trickle process (FIG. 3). A total of 2,750 g of the strongly acidic cation exchange resin were used as a catalyst. In these experiments the isobutene-containing $C_4$ hydrocarbon mixture and the process water were charged together through line 41 and 44, resp., to the top of reactor A, while aqueous TBA and the raffinate were withdrawn through line 48 and 49, resp., at the sump of reactor D. Reaction conditions, materials flows, and results have been compiled in Table 4.

TABLE 4

| (Comparison Examples) |  |  |  |  |
| --- | --- | --- | --- | --- |
|  |  | Experiment | | |
|  |  | 18 | 19 | 20 |
| Temperature, | °C. | 70 | 92 | 98 |
| Pressure, | bar | 16 | 16 | 16 |
| Isobutene content, | mole % | 45 | 45 | 45 |
| n-Butenes content, | mole % | 40 | 40 | 40 |
| Butanes, | mole % | 15 | 15 | 15 |
| Process water quantity (Stream 44), | g/h | 8000 | 8000 | 4000 |
| $C_4$ hydrocarbon quantity (Stream 41), | g/h | 600 | 600 | 600 |
| Isobutene quantity, | mole/h | 4.8 | 4.8 | 4.8 |
| Isobutene conversion, | mole % | 54 | 62 | 68 |
| n-Butenes conversion, | mole % | 0.2 | 1.5 | 1.8 |
| Selectivity for TBA, | mole % | 99.6 | 97.4 | 97.0 |
| Selectivity for SBA, | mole % | 0.35 | 2.3 | 2.6 |
| Selectivity for dimeric compounds | mole % | 0.05 | 0.3 | 0.4 |
| TBA in residual gas, (Stream 49), | wt. % | 12.8 | 24.1 | 28.9 |
| SBA in residual gas, (Stream 49) | wt. % | <0.1 | 0.35 | 0.4 |

We claim:

1. In a direct hydration process for the production of tertiary alcohols having 4 to 5 carbon atoms by reacting a $C_4$–$C_5$ isoolefin-containing hydrocarbon stream with an aqueous stream in an interconnected series of reactors or reaction zones in the presence of a strongly acidic, solid hydration catalyst, the improvement which comprises charging said isoolefin-containing hydrocarbon stream to one end of said series of interconnected reactors and charging said aqueous stream to the opposite end of said series of interconnected reactors and directing said streams through said series of reactors so that the hydrocarbon stream and the aqueous stream flow in opposite directions with respect to said series of interconnected reactors and flow in parallel streams through each individual reactor.

2. A process according to claim 1 in which said reaction is conducted in a series of 2 to 10 interconnected reactors.

3. A process according to claim 1 in which said reaction is conducted in a series of 3 to 5 interconnected reactors.

4. A process according to claim 1 in which said hydrocarbon stream is fed to the sump of the first reactor in said series and said aqueous stream is fed to the sump of the last reactor in said series and an aqueous stream is withdrawn from the upper zone of each reactor and is fed to the sump of the preceding reactor and a hydrocarbon stream is withdrawn from the top of each reactor and fed to the sump of the following reactor.

5. A process according to claim 1 in which said hydrocarbon stream is fed to the top of the first reactor in said series and said aqueous stream is fed to the top of the last reactor in said series and an aqueous stream is withdrawn from the sump of each reactor and is fed to the top of the proceding reactor, and a hydrocarbon stream is withdrawn from the lower zone of each reactor and is fed to the top of the following reactor.

6. A process according to claim 1 in which said process is conducted in a vertical column having a plurality of reaction zones located one above the other.

7. A process according to claim 1 in which said reaction is conducted at a temperature in the range of 30° to 150° C. and a pressure ranging from about 10 to 50 bar.

8. A process according to claim 1 characterized by using the process water or part thereof to free the residual gas from the tertiary alcohol by washing.

9. A process according to claim 1 characterized by removing secondary alcohol formed as a byproduct from the distillation column as a side stream during azeotrope formation of the tertiary alcohol.

10. A process according to claim 9 characterized by locating the lateral tap for the side stream 1 to 7 trays above the tray for feeding the aqueous product alcohol.

11. A process according to claim 1 in which said reaction is conducted in the presence of an acidic cation exhange resin catalyst.

12. In a direct hydration process for the production of tertiary alcohols having 4 to 5 carbon atoms by reacting a $C_4$–$C_5$ isoolefin-containing hydrocarbon stream with an aqueous stream in an interconnected series of reactors or reaction zones in the presence of an solid acidic hydration catalyst, the improvement which comprises operating with two series of interconnected reactors and first charging said isoolefin-containing hydrocarbon stream as well as a first aqueous stream to one end of the first series of reactors in parallel flow and then charging the residual gas still containing isoolefin of the first series of reactors to one end of the second series of reactors and charging a second aqueous stream to the opposite end of said second series of reactors and directing said streams through said series of reactors so that the hydrocarbon stream and the second aqueous stream flow in opposite directions with respect to the second series of interconnected reactors and flow in parallel streams through each individual reactor.

* * * * *